US006876724B2

(12) United States Patent
Zhou et al.

(10) Patent No.: US 6,876,724 B2
(45) Date of Patent: Apr. 5, 2005

(54) LARGE-AREA INDIVIDUALLY ADDRESSABLE MULTI-BEAM X-RAY SYSTEM AND METHOD OF FORMING SAME

(75) Inventors: Otto Z. Zhou, Chapel Hill, NC (US); Jianping Lu, Chapel Hill, NC (US); Qi Qiu, Chapel Hill, NC (US)

(73) Assignee: The University of North Carolina - Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/051,183

(22) Filed: Jan. 22, 2002

(65) Prior Publication Data

US 2002/0094064 A1 Jul. 18, 2002

Related U.S. Application Data

(63) Continuation-in-part of application No. 09/679,303, filed on Oct. 6, 2000.

(51) Int. Cl.[7] .............................................. H01J 36/06
(52) U.S. Cl. ...................................... 378/122; 378/119
(58) Field of Search ................................ 378/122, 126, 378/143, 9–11, 119, 4; 313/309–311

(56) References Cited

U.S. PATENT DOCUMENTS

| | | | |
|---|---|---|---|
| 3,921,022 A | | 11/1975 | Levine |
| 4,253,221 A | | 3/1981 | Cochran, Jr. et al. |
| 4,289,969 A | | 9/1981 | Cooperstein et al. |
| 4,958,365 A | | 9/1990 | Sohval et al. |
| 5,305,363 A | * | 4/1994 | Burke et al. .................... 378/4 |
| 5,377,249 A | * | 12/1994 | Wiesent et al. ................ 378/4 |
| 5,424,054 A | | 6/1995 | Bethune et al. |
| 5,773,921 A | * | 6/1998 | Keesmann et al. ......... 313/309 |
| 6,259,765 B1 | * | 7/2001 | Baptist ....................... 378/136 |
| 6,277,318 B1 | | 8/2001 | Bower et al. |
| 6,280,697 B1 | | 8/2001 | Zhou et al. |
| 6,333,968 B1 | * | 12/2001 | Whitlock et al. ........... 378/136 |
| 6,385,292 B1 | | 5/2002 | Dunham et al. |
| 6,456,691 B2 | * | 9/2002 | Takahashi et al. .......... 378/122 |
| RE38,223 E | | 8/2003 | Keesmann et al. |
| 2003/0002627 A1 | | 1/2003 | Espinosa et al. |

OTHER PUBLICATIONS

A. Thess et al., "Crystalline Ropes of Metallic Carbon Nanotubes," *Science* 273, 483–487 (Jul. 26, 1996).
C. Bower et al., "Synthesis and structure of pristine and alkali–metal–intercalated single–walled carbon nanotubes," *Appl. Phys. A* 67, 47–52 (1998).
X.P. Tang et al., "Electronic Structures of Single–Walled Carbon Nanotubes Determined by NMR," *Science*, vol. 288, 492–494 (Apr. 21, 2000).
C. Journet et al., "Large–scale production of single–walled carbon nanotubes by the electric–arc technique," *Nature*, vol. 388, 756–760 (Aug. 21, 1997).

(Continued)

*Primary Examiner*—David V. Bruce
*Assistant Examiner*—Hoon Song
(74) *Attorney, Agent, or Firm*—Burns, Doane, Swecker & Mathis, L.L.P.

(57) ABSTRACT

A structure to generate x-rays has a plurality of stationary and individually electrically addressable field emissive electron sources with a substrate composed of a field emissive material, such as carbon nanotubes. Electrically switching the field emissive electron sources at a predetermined frequency field emits electrons in a programmable sequence toward an incidence point on a target. The generated x-rays correspond in frequency and in position to that of the field emissive electron source. The large-area target and array or matrix of emitters can image objects from different positions and/or angles without moving the object or the structure and can produce a three dimensional image. The x-ray system is suitable for a variety of applications including industrial inspection/quality control, analytical instrumentation, security systems such as airport security inspection systems, and medical imaging, such as computed tomography.

78 Claims, 8 Drawing Sheets

OTHER PUBLICATIONS

A.M. Cassell et al., "Large Scale CVD Synthesis of Single-Walled Carbon Nanotubes," *J. Phys. Chem. B* 103, 6484–6492 (Jul. 20, 1999).

U.S. Appl. No. 09/296,572, Bower et al., "Device Comprising Carbon Nanotube Field Emitter Structure and Process for Forming Device", filed Apr. 22, 1999.

U.S. Appl. No. 09/351,537, Bower et al., "Device Comprising Thin Film Carbon Nanotube Electron Field Emitter Structure", filed Jul. 1, 1999.

U.S. Appl. No. 09/594,844, Zhou et al., "Nanostructure-Based High Energy Capacity Material", filed Jun. 15, 2000.

U.S. Appl. No. 09/679,303, Zhou et al., "X–Ray Generating Mechanism Using Electron Field Emission Cathode", filed Oct. 6, 2000.

U.S. Appl. No. 09/817,164, Stoner et al., "Coated Electrode with Enhanced Electron Emission and Ignition Characteristics", filed Mar. 27, 2001.

* cited by examiner

LARGE-AREA INDIVIDUALLY ADDRESSABLE MULTI-BEAM X-RAY SYSTEM AND METHOD OF FORMING SAME

CONTINUATION DATA

This is a continuation-in-part of U.S. patent application Ser. No. 09/679,303, filed Oct. 6, 2000 entitled "X-Ray Generating Mechanism Using Electron Field Emission Cathode", the disclosure of which is incorporated herein by reference in its entirety.

STATEMENT REGRADING FEDERALLY SPONSORED RESEARCH OR DEVELOPMENT

At least some aspects of this invention were made with Government support under contract no. N00014-98-1-05907. The Government may have certain rights in this invention.

FIELD OF THE INVENTION

The present invention relates to a method and device for generating and controlling x-ray radiation. For example, the present invention relates to a method and device that generates electron emission from an array or matrix of emitters. Emitted electrons directly impact different locations on a large-area target to produce multiple x-ray beams from different origins and thereby providing improved imaging capabilities, including dynamic imaging.

BACKGROUND OF THE INVENTION

In the description of the background of the present invention that follows reference is made to certain structures and methods, however, such references should not necessarily be construed as an admission that these structures and methods qualify as prior art under the applicable statutory provisions. Applicants reserve the right to demonstrate that any of the referenced subject matter does not constitute prior art with regard to the present invention.

The term "nano-structured" or "nanostructure" material is used by those familiar with the art to designate materials including nanoparticles with a particle size or less than 100 nm, such as nanotubes (e.g.—carbon nanotubes). These types of materials have been shown to exhibit certain properties that have raised interest in a variety of applications.

Current x-ray tubes comprise a target with a single (or dual) focal point(s) (where electrons bombard a target and x-rays are emitted), and either a single cathode or dual cathodes. Electrons are generally thermionically emitted from the cathode(s) and are focused to impact a small area on the target. For imaging or diagnostic purposes over a large area, either the object or the x-ray tube (or both) has to be moved over the area.

Figures 1A, 1C:
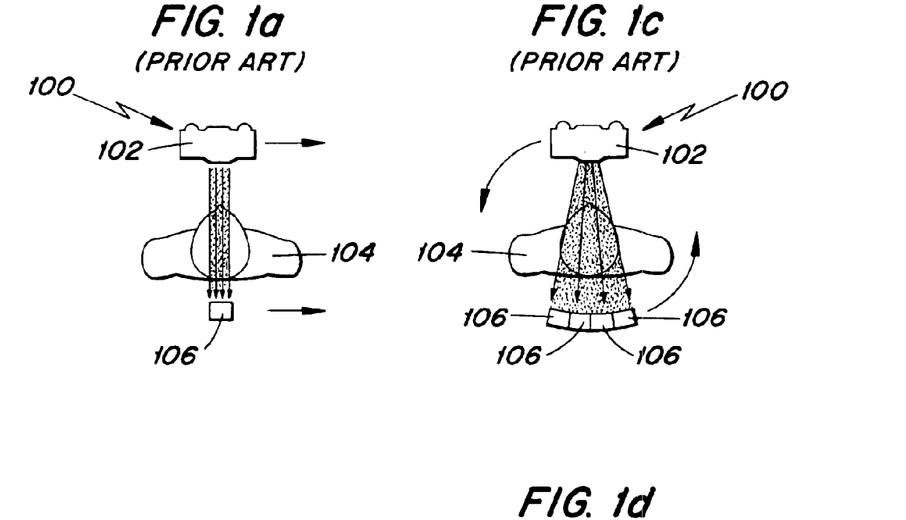
FIGS. 1(a)–(d) represent computed tomography systems in which the x-ray source and/or the detector are rotated about an object to be imaged.
Figure 1B:
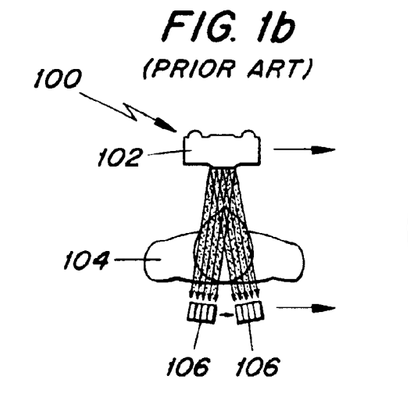
Figure 1D:
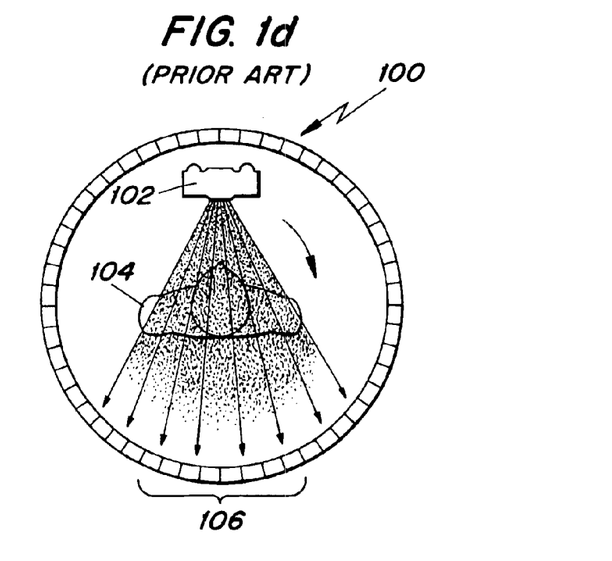

One example of such a use for x-rays includes computed tomography (CT). FIGS. 1 (a–d) depict the general arrangement of a CT scanner 100 in which an x-ray source 102 (typically an x-ray tube) is rotated (direction indicated by the arrow) about the object to be imaged 104. The data can be collected by either a single detector 106 coordinately moving with the x-ray source 102 (see FIG. 1a), multiple detectors 106 coordinately moving with the x-ray source 102 (see FIGS. 1b and 1c), or multiple stationary detectors 106 (see FIG. 1d). As a consequence of the current CT designs, the scanners are usually large with complicated mechanical systems. Scanners can be limited by the rotation speed of the x-ray tube and by the size and weight of the apparatus. This last limitation can adversely affect the capture of clear images of moving parts, such as a beating heart.

Figure 2:
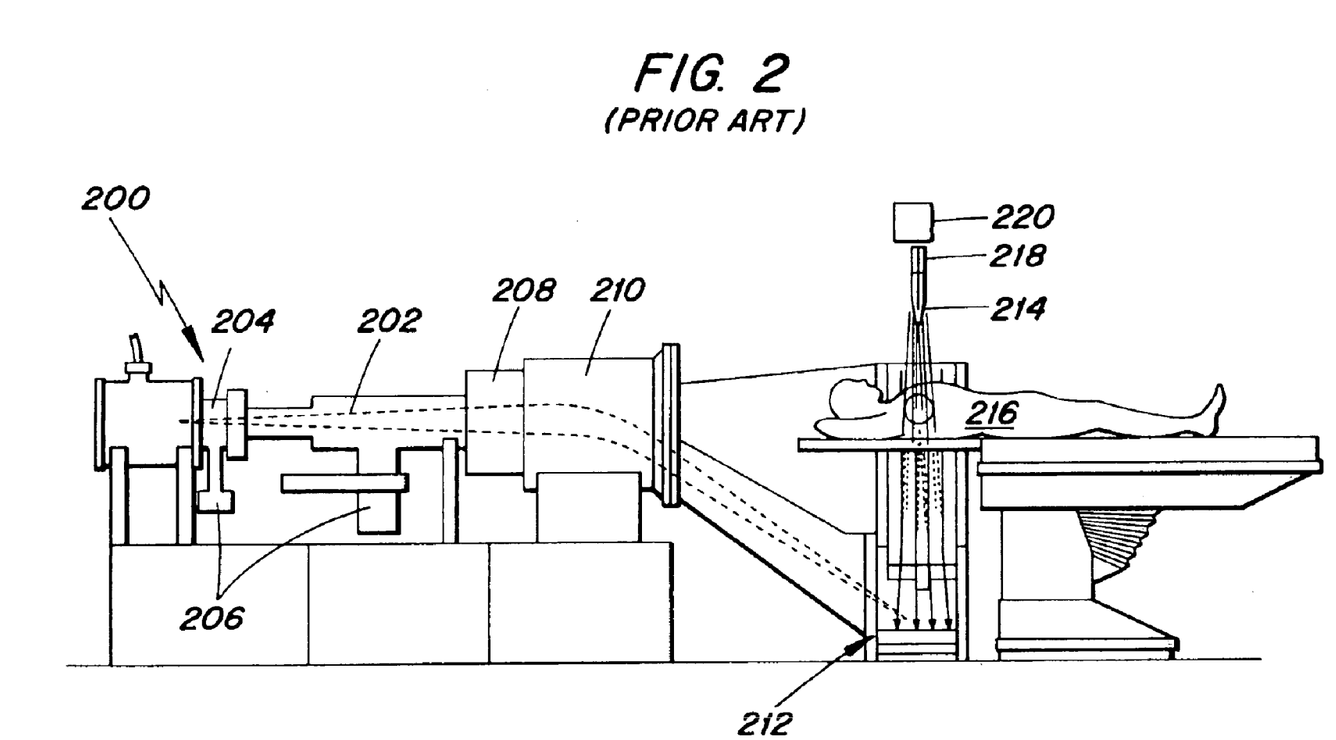
FIG. 2 is a representative example of a fifth generation computed tomography system.

Dynamic three-dimensions (3D) images can be acquired by so-called "fifth generation CT scanners." An example of a $5^{th}$ generation CT scanner 200 is shown in FIG. 2. An electron beam 202 is produced by a stationary electron gun 204 in a vacuum system 206. The electron beam 202 is focused by a focus coil 208 and scanned by a deflection coil 210 such that the applied magnetic field positions the electron beam 202 across any one of several stationary metal target rings 212 from which an x-ray is emitted. The emitted x-rays 214 project toward the object 216 to be imaged and are detected by a stationary detector 218 and processed by a data acquisition system 220. Although such a system is capable of producing dynamic 3D images, the scanner 200 is very large and costly to fabricate.

In addition to the design limitations of current CT scanners, current x-ray sources use heated metal filaments as the sources of electrons. Because of the thermionic emission mechanism, a very high operating temperature is required, typically in the order of 1000–1500° C. The high operating temperatures results in problems such as short lifetime of the filament, slow response time (i.e., time to warm up the filament before emission), high-energy consumption, and large device size.

Further, because of the fundamental physics of the thermionic emission mechanism, electrons are emitted in all directions. In x-ray tube applications, an additional electrical field can be applied to bring the electrons into focus at the target, but with attendant complexity and cost. Additionally, such conventional techniques of focusing electron beams have certain disadvantages, such as limits on the uniformity and size of the focusing spots.

Carbon nanotube materials have been shown to be excellent electron field emission materials. In this regard, carbon nanotube materials have been shown to possess low electron emission threshold applied field values, as well as high emitted electron current density capabilities, especially when compared with other conventional electron emission materials.

Commonly owned U.S. Pat. No. 6,630,772 (Ser. No. 09/296,572 entitled "Device Comprising Carbon Nanotube Field Emitter Structure and Process for Forming Device") the disclosure of which is incorporated herein by reference, in its entirety, discloses a carbon nanotube-based electron emitter structure.

Commonly owned U.S. Pat. No. 6,552,380 (Ser. No. 09/351,537 entitled "Device Comprising Thin Film Carbon Nanotube Electron Field Emitter Structure"), the disclosure of which is incorporated herein by reference, in its entirety, discloses a carbon-nanotube field emitter structure having a high emitted current density.

Commonly owned U.S. Pat. No. 6,277,318 entitled "Method for Fabrication of Patterned Carbon Nanotube Films," the disclosure of which is incorporated herein by reference, in its entirety, discloses a method of fabricating adherent, patterned carbon nanotube films onto a substrate.

Commonly owned U.S. Pat. No. 6,553,096 (Ser. No. 09/679,303 entitled "X-Ray Generating Mechanism Using Electron Field Emission Cathode"), the disclosure of which is incorporated herein by reference, in its entirety, discloses an X-ray generating device incorporating a nanostructure-containing material.

Thus, there is a need in the art to address the above-mentioned disadvantages associated with methods and devices for generating x-rays and for applying x-rays in applications in imaging environments, such as computed tomography. Further, there is a need in the art for imaging solutions in both static and dynamic environments.

SUMMARY OF THE INVENTION

A structure to generate x-rays with a target and an opposing surface has a plurality of stationary and individually electrically addressable electron sources defining a plurality of cathodes. The structure to generate x-rays can be an x-ray source in a device to record x-ray images. The electron source is preferably a field emission electron source and can be a triode-type having a substrate composed of a field emissive material and a gate electrode positioned parallel to and insulated from the substrate. The field emissive material is preferably a material that has a low threshold field for emission and is stable at high emission currents. For example, the field emissive material can be carbon nanotubes such as single wall, double wall, or multi-wall carbon nanotube, nanowires or nanorods of metal, metal oxide, silicon, silicon oxide, carbide, boride, nitride, or chalcogenide. Additionally, nanostructure containing materials formed from silicon, germanium, aluminum, silicon oxide, germanium oxide, silicon carbide, boron, boron nitride, and boron carbide can be the field emissive material. The cathodes and the target are housed in an evacuated chamber with multiple windows that are transparent to x-rays.

The electrons emitted from the stationary cathodes are accelerated to and impact on different points of the target by the voltage applied between the target and the cathodes. The target area or a particular target from amongst multiple targets where an electron impacts can be controlled or selected by a suitable design of cathodes and target geometry, or by applying additional focusing electric fields, or other suitable techniques. Upon impact by the electrons, x-ray radiation is emitted from the impact surface of the target materials. Direction and divergence of the x-ray radiation can be controlled by the location of the windows and collimators with respect to the chamber.

The intensity of the x-ray radiation depends on the voltage applied between the target and the cathode, and the emitted electron current. The emitted electron current from the emissive materials is controlled by the electrical field between the gate electrode and the field emissive material in the triode configuration or between the target and the field emissive material in the diode case. The field emitted electrons are essentially non-divergent and travel toward the gate electrode and anode. The emission can occur at 300K and can be rapidly switched on and off by controlling the electric field applied.

In one embodiment, a method of generating an x-ray image positions an object within an imaging zone, switches each of a plurality of cathodes on a stationary cathode structure at a predetermined frequency to field emit an electron, emits an x-ray from a target of the stationary target structure at the predetermined frequency, images the object, and detects the emitted x-ray. Each of the plurality of cathodes comprises a field emissive electron source is individually addressable and electrically switched in a programmable sequence to field emit electrons toward an incidence point on a stationary target structure.

In another embodiment, a method for obtaining an x-ray image places an object in an x-ray source, applies power to at least one of the plurality of cathodes to generate x-ray radiation for a pre-set or variably-set exposure time, exposes the object to the x-ray radiation, and captures an x-ray image corresponding to the object by either an x-ray detector or an x-ray sensitive film.

In one aspect, the x-ray detector or x-ray sensitive film moves at a corresponding frequency to the pre-set or variably-set frequency applied to the cathode to capture an image and/or detect an x-ray. Alternatively, the x-ray detector or x-ray sensitive film is stationary and the individual, group, or portions of the individual or group of x-ray detectors or x-ray sensitive films are activated (e.g., enabled to detect and/or capture) at a corresponding frequency to the pre-set or variably-set frequency applied to the cathode to capture an image and/or detect an x-ray.

In a further aspect, the position on the stationary target structure from which the x-ray emits corresponds spatially and temporally to a position on the cathode structure from which the electron emits and at least one of a circumferential position and an elevation angle of the emitted x-ray is sufficiently discriminated with respect to the object to produce a three dimensional image.

In an additional aspect, power is applied to all of the plurality of cathodes simultaneously or to a subset of the plurality of cathodes sequentially at a pre-set or variably-set frequency. In the latter, the x-ray detector or the x-ray sensitive film is moved or activated at a corresponding frequency to the pre-set or variably-set frequency to capture the x-ray image. The frequency can be sufficiently rapid to dynamically image a physiological function.

The x-ray system can have a large-area target and an array or matrix of emitters. Electrons are emitted directly towards different incidence points on the target to produce multiple x-ray beams from different origins. The result is that images of a large object can be taken from different areas and/or angles without moving the object or the x-ray tube. The x-ray system is suitable for a variety of applications including industrial inspection/quality control, analytical instrumentation, security systems such as airport security inspection systems, and medical imaging, such as computed tomography.

BRIEF DESCRIPTION OF THE DRAWING FIGURES

Other objects and advantages of the invention will become apparent from the following detailed description of preferred embodiments in connection with the accompanying drawings in which like numerals designate like elements and in which.

DETAILED DESCRIPTION OF THE PREFERRED EMBODIMENTS

A structure to generate x-rays comprises a plurality of stationary and individually electrically addressable electron sources defining a plurality of cathodes, at least one target placed opposing the cathodes, and an evacuated chamber that houses the plurality of cathodes and the at least one target. The electron sources can be filed emission electron sources and can be triode-type or diode-type structures.

Figure 3:
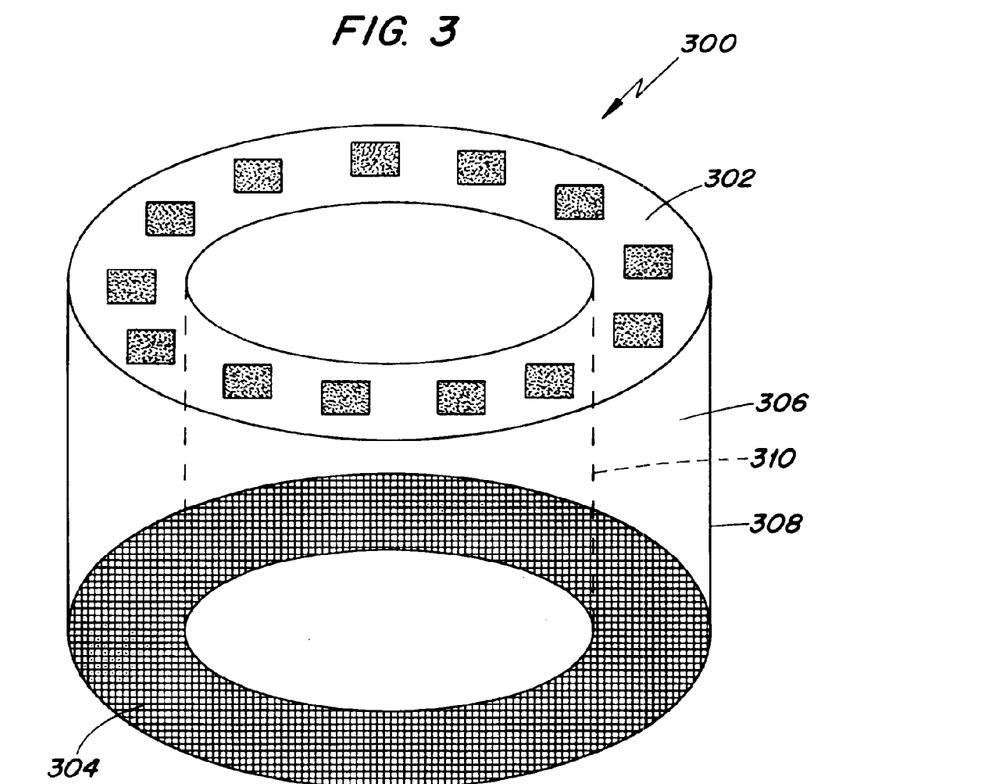
FIG. 3 is an embodiment of a structure to generate x-rays.

FIG. 3 is an embodiment of a structure 300 to generate x-rays. A cathode structure 302 and a target structure 304 are disposed within a chamber 306, which is substantially in the form of a hollow cylinder having an outer wall 308 and an inner wall 310. The cathode structure 302 and the anode structure 304 are positioned within the chamber 306 between the inner wall 308 and the outer wall 310. The chamber 306 is operationally maintained at a vacuum of at least 1 Torr by a suitable vacuum system operatively connected to the chamber 306. Feedthroughs (not shown), as known in the art, can provide services to components within the chamber 306.

A device to record x-ray images comprises an x-ray source having a cathode structure and a target structure, an object positioning system and a detector system. In one aspect the x-ray source can be a structure to generate x-rays as shown and described herein.

Figure 4:
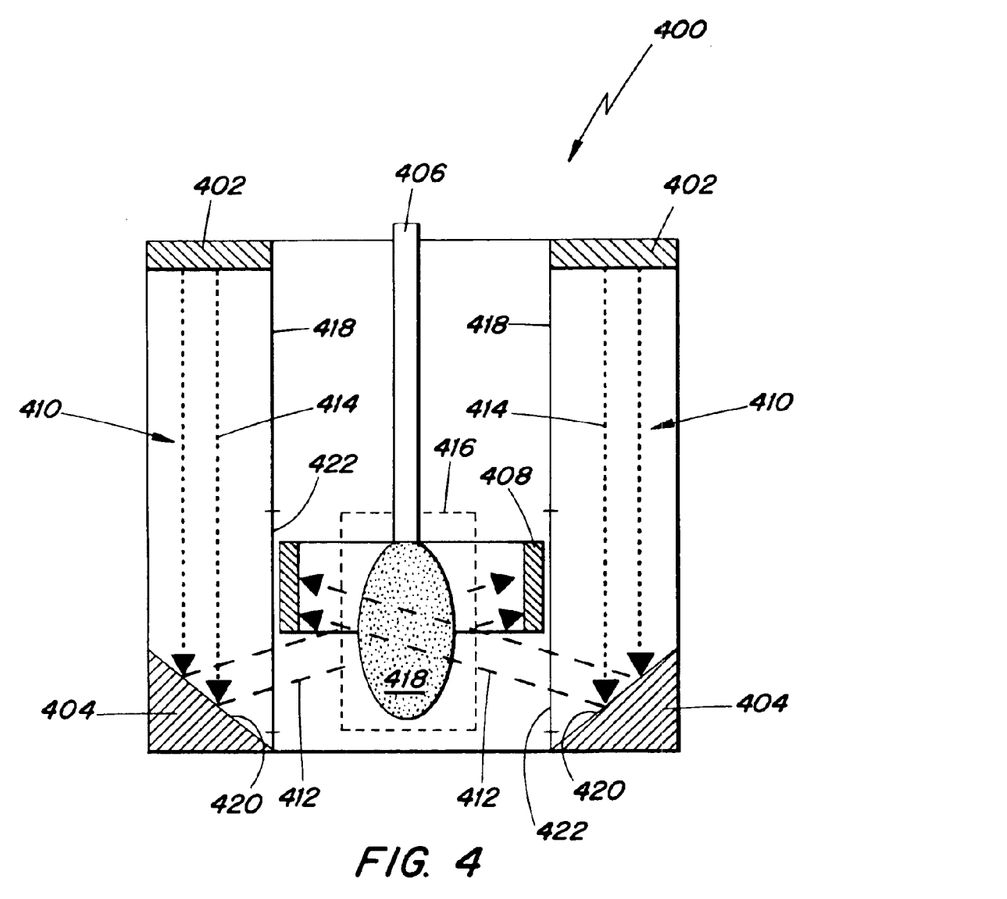
FIG. 4 a cross sectional view of an embodiment of a device to record x-ray images.

On example of an embodiment of a device to record x-ray images is shown in FIG. 4 in cross sectional view. The device 400 to record x-ray images has a cathode structure 402, a target structure 404, an object positioner 406, and a detector 408. The cathode structure 402 can be in the form of a single cathode or a plurality of cathodes. In the embodiment shown, the cathode structure 402 is arranged as a ring to correspond to the overall shape of the chamber 410. Similar to the cathode structure 402, the target structure 404 can be in the form of a single target or a plurality of targets. In the embodiment shown, the target structure 404 is arranged as a ring to correspond to the overall shape of the chamber 410. The target structure 404 can produce an x-ray 412 of a desired wavelength upon bombardment by electrons 414 emitted from the cathode structure 402. The x-ray 412 propagates to an imaging zone 416 containing the object 418 to be imaged and is detected by the detector 408. The detector 408 can be an array or matrix of x-ray detectors or x-ray sensitive films opposing the x-ray source, the array or matrix substantially parallel to and at equal distance to the x-ray source (e.g. the position from which x-rays propagate to the object). In one aspect, the detector 408 can be located on the circumference of the imaging zone 416 adjacent to the inner wall 418 and outside of the chamber 410. In another aspect, the x-ray sources and detectors can be on opposing parallel planes. The device 400 to record x-ray images is suitable for a variety of applications including industrial inspection/quality control, analytical instrumentation, security systems such as airport security inspection systems, and medical imaging, such as computed tomography.

The cathode structure 402 can be any suitable geometric form having a surface 420 facing the target structure 404. For example, the cathode structure 402 can be substantially an annulus, a torus, or a plate. One or more, field emissive electron sources can be affixed to the cathode structure 402.

Where the cathode structure is a plane or is planar-like, the plurality of cathodes and the at least one target can be each on an opposing plane and he target has a deflection surface that can be oriented toward a surface of the plurality of cathodes that emits electrons. In one aspect the deflection surface is oriented non-parallel to the surface of the plurality of cathodes. Further, each of the plurality of cathodes can be individually positioned on one of the opposing planes at a pre-determined spatial interval.

Where the cathode structure is a ring or is ring-like, the plurality of cathodes can be disposed on a first ring and the at least one target can be disposed on a second ring, the first and second rings concentric, and the at least one target has a deflection surface that can be oriented toward a surface of the plurality of cathodes that emits electrons. In one aspect, the deflection surface can be oriented non-parallel to the surface of the plurality of cathodes. Further, each of the plurality of cathodes can be individually positioned on one of the first or second rings at a pre-determined spatial interval.

Figure 5:
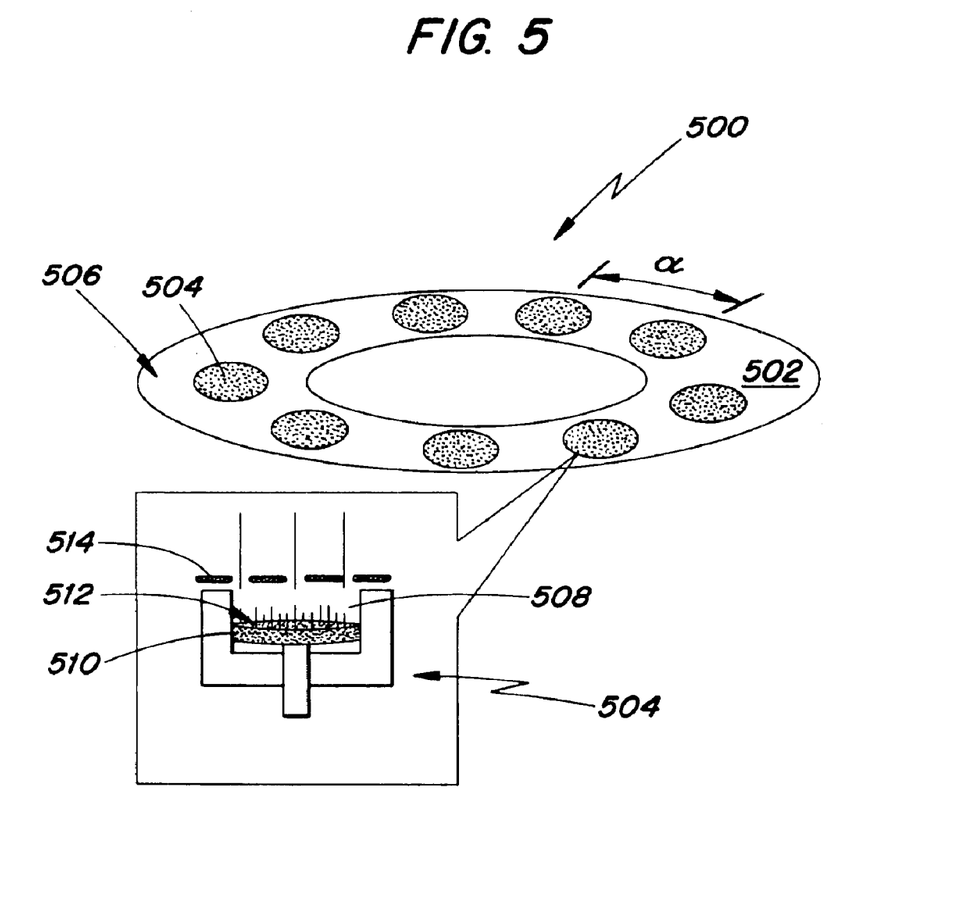
FIG. 5 is an embodiment of a cathode structure.

FIG. 5 shows an exemplary embodiment of a cathode structure 500 as substantially an annulus 502 with multiple discreet field emissive electron sources 504 disposed on a broad facing surface 506. Each field emissive electron source 504 defines a cathode in an x-ray generating apparatus. The field emissive electron sources 504 are each individually electrically addressable and stationarily affixed to the cathode structure 500. In the FIG. 5 embodiment, the field emissive electron sources 502 are arranged at intervals along the cathode structure 500. The interval ($\alpha$) can be any suitable interval to obtain the desired imaging results. Both fixed intervals and random intervals are envisioned. In at least one exemplary embodiment, the interval between successive field emissive electron sources 504 is approximately 10°.

In the FIG. 5 embodiment, a recess 508 in the cathode structure 500 can house a planar circular field emissive material 510. Disposed parallel to the planar surface 512 of the field emissive material 510 and insulated from it is a gate electrode 514. Further, the gate electrode 514 can be disposed across a surface of the field emissive material 510 substantially equidistant from the field emissive material 510. The arrangement of field emissive material and gate electrode can be, for example, a triode-type or diode-type structure. When above a threshold value, a bias (e.g., electric field) between the field emissive material 510 and the gate electrode 514 extracts and accelerates electrons from the cathode substantially perpendicularly to the planar surface 512 of the field emissive material 510. Accordingly, the field emitted electrons are non-divergent. The plurality of field emitted electrons pass the gate electrode and are further directed to a predetermined position and accelerated to impact on the at least one target by the electric field applied between the gate electrode and the at least one target. Upon impact at an incidence point, at least one x-ray having a characteristic wavelength corresponding to a material of the at least one target and at least one x-ray having a continuous wavelength are generated.

The field emissive material 510 can be formed from any one of numerous nanostructure materials that possess high emission current densities. For example, the field emissive material can be carbon nanotubes (e.g., single walled carbon nanotubes, double walled carbon nanotubes, or multi-wall carbon nanotubes). Alternatively, the field emissive material can be a nanotube comprising at least one non-carbon element. Further, the field emissive material can be a nanorod/nanowire comprising at least one of a metal, a metal oxide, silicon, silicon carbide, silicon oxide, carbon nitride, boron nitride, boron carbide, or a chalcogenide or can be other nanowires such as SiC or SiC nanowires. Additionally, nanostructures containing materials formed from silicon, germanium, aluminum, silicon oxide, germanium oxide, silicon carbide, boron, boron nitride, and boron carbide are contemplated. More specific details of the above-mentioned materials are disclosed in commonly owned U.S. Pat. No. 6,334,939; (Ser. No. 09/594,844; the disclosure of which is incorporated herein by reference in its entirety.

Figure 9:
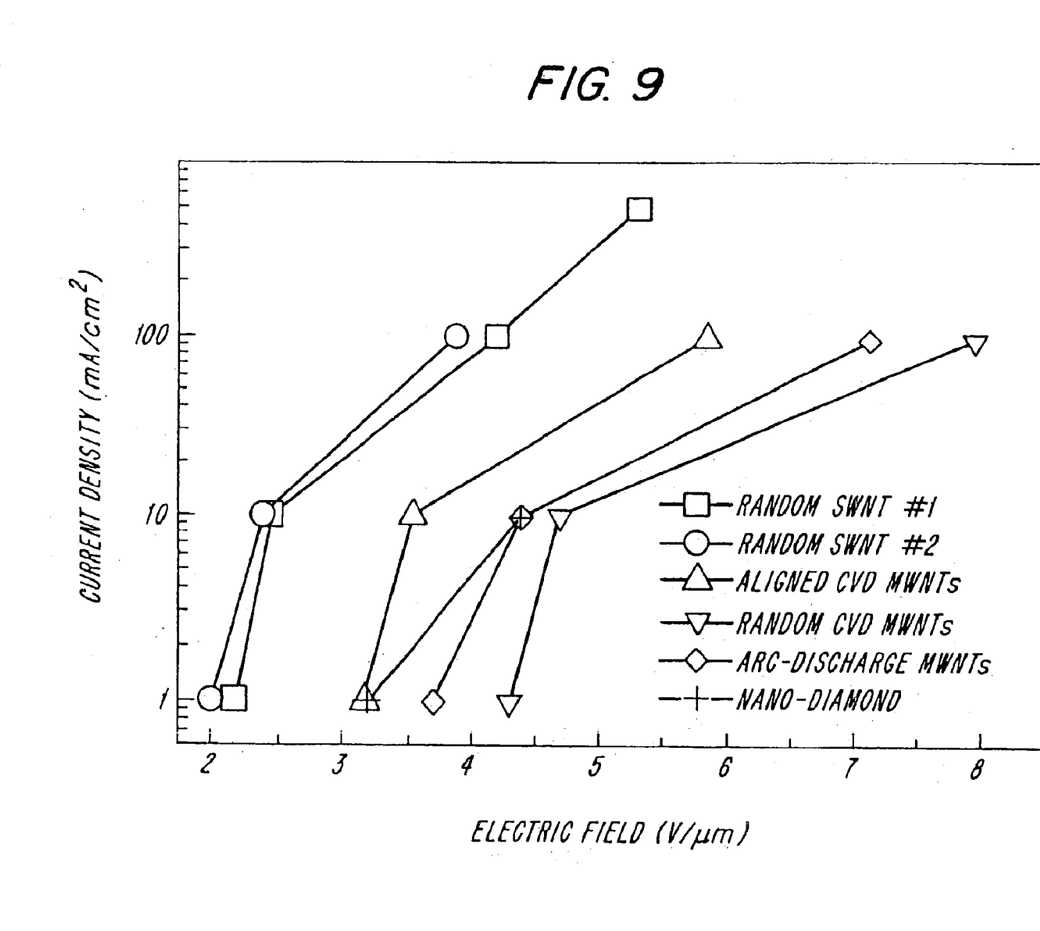
FIG. 9 is a graph depicting the threshold field required to obtain a certain emitted current density for several field emission materials.

Field emission measurements have been made on various single wall and multi-wall nanotube materials formed according to the principles of the present invention. FIG. 9 depicts graphically five nanotube materials prepared in accordance with this invention. These measurements show current density of 10 mA/cm² at an applied electrical field of 2–5 V/μm and 100 mA/cm.sup.2 or greater at an applied electrical field of 4–7 V/μm. The results from a nano-diamond field emission material is shown for comparison. As illustrated by FIG. 9, the investigated materials exhibit a relatively high current density under a relatively low applied electrical field voltage.

The field emissive material can be applied by any suitable technique and in any suitable geometric form. Examples of suitable techniques and forms are given in commonly owned U.S. Pat. No. 6,277,318, entitled "Method for Fabrication of Patterned Carbon Nanotube Films," the disclosure of which is incorporated herein by reference, in its entirety, in which a method of fabricating adherent, patterned carbon nanotube films onto a substrate is disclosed. Further, it is known to form field emitting cathodes with various geometrical configurations, such as one or more sharp points or ridges which act to focus the beam of emitted electrons. See, for example, U.S. Pat. Nos. 3,921,022; 4,253,221; and 5,773,921, the disclosures of which are incorporated herein by reference. Additional suitable techniques include coating the field emissive material on the substrate as a film, embedding the field emissive material in a matrix of the substrate, or forming the field emissive material as a free-standing substrate structure.

In an additional embodiment, the cathode structure can be a suitable structural substrate material coated with a field emissive material and formed into the field emissive electron source. In this embodiment, the cathode structure can be formed as a continuous array or a matrix of field emissive materials and can be individually electrically addressable. For example, the structural material can have an interdigitated array (IDA) of conductors with discrete surface areas exposed on the surface of the upper ring. Interdigitated arrays can be fabricated for specific applications by photolithographic techniques and using a lift-off process. Additionally, IDAs are commercially available in standard forms from, for example, ABTECH Scientific, Inc., Richmond Va. A layer of field emissive material, such as single wall, double wall nanotubes, or multi-wall nanotubes, can be disposed on the structural material and can cover the discrete areas corresponding to exposed electrical leads of the IDA. By electrically addressing the discrete areas individually or in programmed sequence, the field emissive material can be pulsed advantageously to produce field emission electrons that can be directed to particular areas on the target. An insulating layer and a gate electrode can be coated on the field emissive material by a physical vapor deposition technique or other suitable technique. Alternatively, the gate electrode can be a separate structure, such as a screen, that can be positioned adjacent the insulating layer either abutting the insulting layer or with a separation distance.

The field emissive electron source or cathode may be formed in any suitable manner. For example, a carbon nanotube film can be formed by depositing carbon nanotubes onto a substrate. The carbon nanotubes can be deposited onto the substrate by any suitable means. An example of a deposition technique includes the use of an adhesion promoting layer. An example of an adhesion promoting layer is disclosed in commonly owned Ser. No. 09/817,164, the disclosure of which is incorporated herein by reference in its entirety.

Numerous single wall nanotube fabrication techniques are envisioned. For example, the single wall nanotubes can be fabricated using a laser ablation process. This technique is generally described, for example, in A. Thess et al., *Science*; 273, 483–487 (1996); C. Bower et al., *Applied Physics*, Vol. A67, 47 (1998); X. P. Tang et al. *Science*, Vol. 288, 492 (2000), the disclosures of which are hereby incorporated by reference. Single wall carbon nanotubes can also be fabricated by arc-discharge (See, for example, C. Journet et al., *Nature*, Vol. 388, 756 (1997)) and chemical vapor deposition techniques (See, for example, A. M. Cassell et al. *J. of Physical Chemistry B*, 103, 6484 (1999)).

One particularly suitable technique of forming single wall nanotubes according to the present invention includes a technique as described in commonly owned U.S. Pat. No. 6,280,697 (Ser. No. 09/259,307; the disclosure of which is incorporated herein by reference, in its entirety.

According to this technique, a target made from graphite and a suitable catalyst, such as nickel and/or cobalt is placed within a quartz tube. The target is formed from a graphite powder mixed with 0.6 atomic percent nickel and 0.6 atomic percent cobalt, and graphite cement. The target is then heated within the tube to a temperature of approximately 1150° C. The tube is evacuated by means of a vacuum pump and a flow of inert gas, such as argon, is introduced into the tube by a suitable source. Various control devices may be attached to the system for controlling and monitoring the flow of inert gas into the tube, as well as the vacuum within the tube. The pressure of the inert gas as is maintained at a suitable level, such as approximately 800 torr.

An energy source, such as a pulsed Nd:YAG laser, is used to ablate the target at the above-described temperature. Preferably, the first and/or second harmonic beam of the laser, i.e. 1064 nm and 532 nm, respectively, are used to ablate the target.

As the target is ablated, nanotube-containing material is transported downstream by the inert gas flow, and forms deposits on the inner wall of the tube. These deposits are then removed to recover the nanotube-containing material. This material, as recovered, has been analyzed and found to contain 50–70 volume % of SWNTs with individual tube diameters of 1.3–1.6 nm and bundle diameters of 10–40 nm. The bundles are randomly oriented.

The as-recovered materials are then purified by a suitable purification process. In a preferred embodiment, the nanotube material is placed in a suitable liquid medium, such as an organic solvent, preferably an alcohol such as methanol. The nanotubes are kept in suspension within the liquid medium for several hours using a high powered ultrasonic horn, while the suspension is passed through a micro porous membrane. In another embodiment, the carbon nanotube containing material is first purified by reflux in a suitable solvent, preferably 20% $H_2O_2$ with subsequent rinsing in $CS_2$ and then in methanol, followed by filtration, as described in Tang et al., *Science*, Vol. 288, 492 (2000).

In addition to the above described processing steps, the purified materials can be further processed by milling, such as ball-milling or oxidation. The optional step of milling will of course act to create even more broken nanotubes and theoretically at least even further increase the number of ends of the nanotubes which are capable of forming sites for the emission of electrons toward an anode target. The carbon nanotubes can also be shortened by oxidation in strong acid. The length of the nanotubes can be controlled by the acid concentration and reaction time. In a preferred embodiment, the purified single wall carbon nanotubes are sonicated in a solution of 3:1 volume ratio of $H_2SO_4$ and $HNO_3$. The average nanotube length is reduced to 0.5 micron (from 10–30 micron in the as purified case) after 24 hours of sonication. More emission tips per unit area can be obtained using the short nanotubes.

Processing methods and considerations in forming an x-ray generating mechanism using field emission cathodes are contained in commonly owned U.S. Pat. No. 6,553,096 (U.S. patent application Ser. No. 09/679,303, the disclosure of which is herein incorporated by reference.

Figure 6:
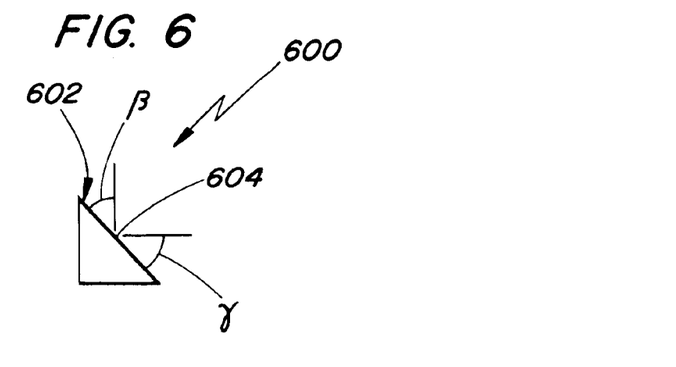
FIG. 6 is a schematic of the details of the target structure.

The target structure can have one or more targets, each corresponding to a field emissive electron source. FIG. 6 shows an exemplary target structure 600 in the form of the target structure cross section of FIG. 4. In the exemplary embodiment shown, the target structure 600 is substantially triangular in form with a deflection surface 602 that generates x-rays from an incidence point 604. The deflection surface 602 is oriented substantially non-perpendicularly to the propagation direction of the accelerated electron beam incident to the deflection surface 602. Accordingly, a non-divergent and accelerated emitted electron from the field emissive electron sources impacts the deflection surface 602 at an incidence point 604 at an angle β such that the emitted x-ray is propagated toward the imaging zone at a corresponding angle γ to the deflection surface 602.

The cathode structure and the target structure can be mounted within the chamber by suitable means. In one embodiment, the cathode structure and target structure are mounted directly to the interior surface of the chamber and are provided with suitable electrical insulation. In another embodiment, ceramic screws connect the upper ring to the lower ring. An additional ceramic screw can be used to affix the lower ring to an interior surface of the chamber. One particularly suitable ceramic screw is approximately 5 cm in length and has insulating properties.

The detector can be any suitable x-ray detecting means. For example, the detector can be a rotatable detector that can be positioned circumferentially to the object to be imaged and opposite to the incidence point of the electron beam on the target structure. In another example, the detector can be an array or matrix of x-ray detectors or x-ray sensitive films stationarily positioned opposite the x-ray source and in line with the image to be detected. The array or matrix can be substantially parallel to and at equal distance to the x-ray source. In a still further example, the detector can be a matrix of detectors stationarily positioned above the plane of the target structure. In this embodiment, the deflection surface of the target is appropriately pitched to generate an x-ray beam that propagates non-planar to the target structure and in a direction that intersects with the matrix of detectors. Further, the array or matrix of x-ray detectors or x-ray sensitive films can detect an x-ray and produce an x-ray image by the interaction of the x-ray with an individual, group, or portions of the individual or group of x-ray detectors or x-ray sensitive films.

In embodiments in which the detector is stationarily mounted, the detector can detect or capture an x-ray image or signal from an emitted x-ray and transfer the image or signal to a computer storage device. Subsequently, the detector is refreshed, thereby prepared to detect/capture the next image. In one example, a suitable detector used in the step of detecting is a charge-coupled device (CCD).

Referring to FIG. 4, a plurality of x-ray transparent windows 422 can be disposed in the inner wall 418 of the chamber 410. The windows 422 can be made of suitable materials, as is known in the art. Additionally, the windows 422 can be operatively positioned with respect to the imaging zone 416 corresponding to the path of the x-rays 412 to allow the passage of at least one x-ray beam generated by the plurality of electrons from a corresponding one of the plurality of cathodes. Further, the windows 422 can provide a collimating feature to the apparatus. The collimating feature arises from the positioning of the window 422 with respect to the propagating path of the generated x-ray.

Field emissive electron sources field emit electrons by applying a bias to a field emissive material and can be individually addressed to emit electrons varying temporally and spatially. The field emissive electron sources or portions thereof can be addressed by a control voltage individually, or in predetermined sequences or groupings, to provide control over the emitted electron beam and so as to direct the beam to impact at any one position on the anode target. By this method, multiple points of incidence on a target may be impacted in the same device. If the target is made from several different materials, a broader spectrum of emitted x-rays can be generated without having to add and remove targets of different materials from the chamber. Additionally, the use of an array of field emissive sources can be used to reduce the time any one area of the target is bombarded, thus contributing to reduced heating of the anode.

For example, in an embodiment in which the cathode structure is circular, the field emissive material can be pulsed in a stepped fashion in which, in every revolution around the cathode structure, the angular distance between field emissive material addressed by successive pulses varies either in a predetermined manner or randomly.

In an additional example, where the field emissive material is positioned on the cathode structure at a desired interval, the field emissive material can be pulsed in successive or non-successive fashion to produce field emission electrons that produce x-rays from the target corresponding in angular position and in pulse frequency to the electrons emitted from the field emissive material. Additionally, the field emissive material can be pulsed individually or in groups, sequentially or randomly, in a clockwise or counter clockwise rotation, or can be pulsed at a predetermined angular separation. Desired intervals can include angular separations from approximately 10° to 120° and can include 10°, 15°, 30°, 45°, 60°, 90°, or 120° or variations thereof.

Further, the cathode can have a rasterization capability. Through the use of individual, group, or matrix addressing of selected regions of the cathode, a rasterized emitted electron beam can be generated and directed to impinge distinctly at a point of incidence on the target. By this arrangement, the stationary cathode can be electrically switched at a predetermined frequency to generate emitted electrons and accelerate them toward a corresponding incident point on a stationary target.

The emitted x-rays from the stationary target accordingly correspond in position and frequency to the electrically switched cathodes and generate emitted x-rays that can be sufficiently discriminated about the object to be imaged so as to produce a three dimensional image. The emitted x-rays are discriminated both in angular position about the object to be imaged and/or by elevation angle with respect to the object to be imaged. Further, the predetermined frequency is sufficiently rapid to dynamically image physiological functions of the object to be imaged. In one example, the power can be applied to all of the plurality of cathodes simultaneously. In another example, power can be applied to a subset (e.g., less than all) of the cathodes sequentially at a frequency and thereby to electrically switch on and off the generation of x-rays. The frequency can be either pre-set or variably-set (e.g., changed in response to a feedback mechanism, either automatically or manually). In one aspect, the frequency can be sufficiently rapid to image the beating of a human heart in a CT application. In an exemplary embodiment, the predetermined frequency in the range of 0.1 Hz to 100 kHz.

Figure 7:
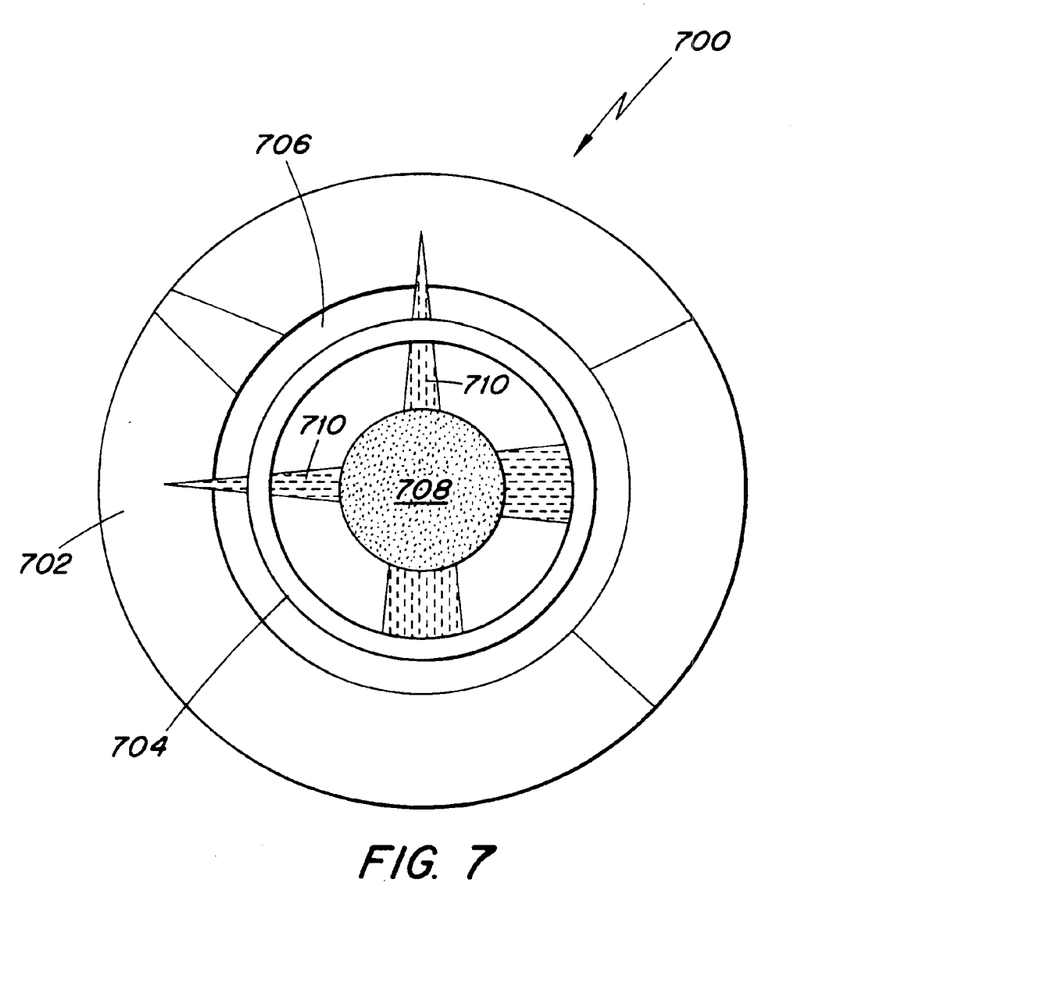
FIG. 7 is a first schematic representation of generated x-rays imaging an object.

FIG. 7 shows a top view of an apparatus for generating x-rays 700 depicting a target structure 702 in a substantially circular form. A detector 704 can be positioned within the hollow 706 of the apparatus 700 and can be adapted to allow positioning of an object 708 within the imaging zone. The detector 704 can be operatively positioned to receive emitted x-rays 710 from the target structure 702 after they have passed through the imaging zone. In the FIG. 7 embodiment, two discrete positions are shown generating x-rays. Although two positions are shown, it is to be understood by one skilled in the art that any number of spatially arranged x-ray generating positions can be utilized. Further, when the cathode is electrically switched, the detector system can be moved or appropriately activated in a corresponding frequency to the frequency of switching the power so as to position or activate the detector to capture the x-ray image.

Figure 8:
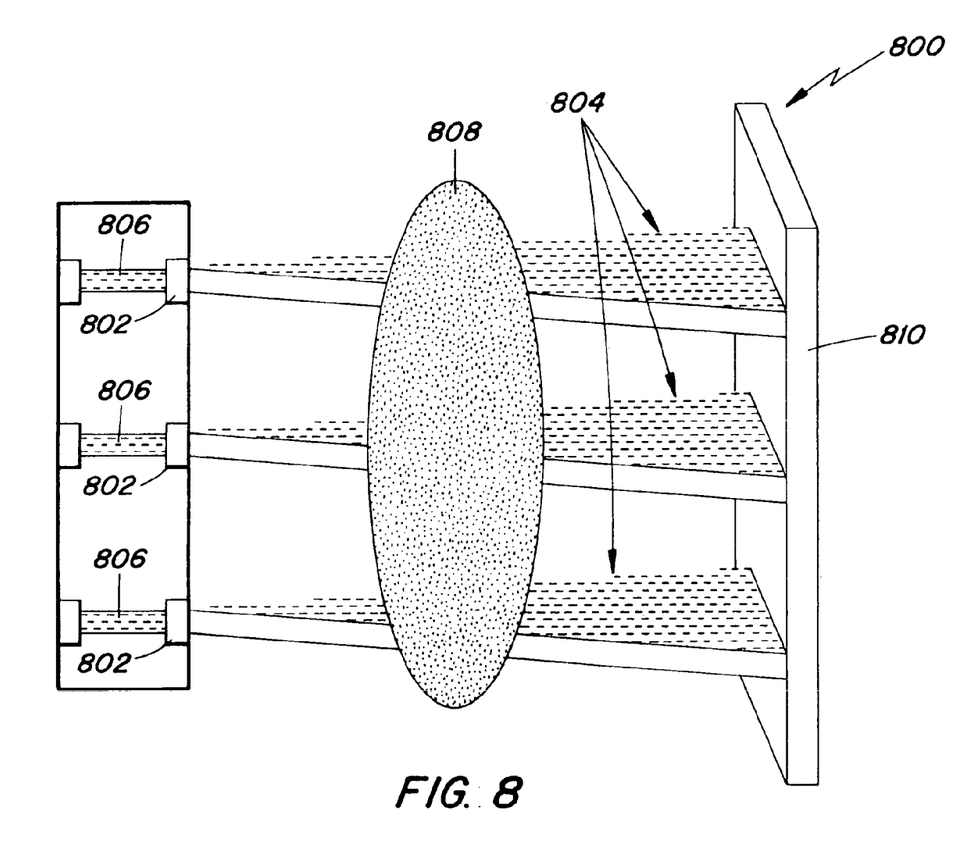
FIG. 8 is second schematic representation of generated x-rays imaging an object.

Additionally, any form of x-ray beam can be generated by the apparatus. For example, an area array of targets can each generate a pencil-like x-ray beam which may correspond to one or more pixels in the detector, preferably no more than ten pixels. Alternately, a line array of target material can each generate a fan-like x-ray beam which corresponds to one or more lines of pixels in the detector, preferably no more than ten lines of pixels. Finally, an area array of targets can each generate a fan-like x-ray beam which corresponds to an area of no more than 128×128 square pixels, preferably no more than 64×64 square pixels. FIG. 8 depicts an embodiment of an apparatus 800 in which the target material 802 generates a fan-like x-ray beam 804 when bombarded by electrons 806. In FIG. 8, the fan-like x-ray beams 804 image the object 808 in transmission mode and impact a large area array detector 810. Accordingly, the detector 810 is individually addressable (e.g., pixilated).

The object positioner adjusts the position of an object to be imaged within the imaging zone. For example, the object positioner can place an object between the x-ray source and the array or matrix of the detector. In one example, the object to be imaged is stationarily mounted onto the object positioner such that a centroid of the object to be imaged is positioned centrally within the imaging zone. In a CT application, the object can be a patient suitably oriented within the imaging zone. Further, the centroid can correspond to the physiological function to be monitored, such as the heart.

A detector is operatively positioned to detect the x-ray after it has passed through the imaging zone. In one embodiment, the detector can be at a elevation angle to the plane defined by the target structure. The angle β and corresponding angle γ can be chosen to cause the emitted x-rays to propagate at an angle out of plane to that of the target structure, such that the propagating x-rays can be detected by a detector positioned so as not to obstruct the field of view of the target, e.g., located above the target structure and across the imaging zone from the origin of the x-rays to be detected. By such an arrangement, the stationarily positioned detector array or matrix does not block the x-ray from the target structure (e.g., obstruct the target with the backside of the detector) and allows simultaneous imaging of the object from all directions (e.g., 360° imaging).

An exemplary method to obtain an x-ray image performed consistent with the present invention stationarily positions an object to be imaged on an object positioner and positions the object to be imaged within an imaging zone, electrically switches a plurality of stationary and individually addressable field emissive electron sources at a predetermined frequency, each field emissive electron source electrically switched in a programmable sequence to field emit electrons toward an incidence point on a stationary target. The beam of field emitted electrons which impact the target generate x-rays by means well known in physics. The generated x-rays then exit the chamber through the collimating windows and image the object to be imaged within the imaging zone. The emitted x-rays are then detected by a suitable detector. The emitted x-rays correspond in position and frequency to the electrical addressing of the field emissive electron sources. Additionally, the circumferential position and/or the elevation angle of the emitted x-rays is sufficiently discriminated with respect to the object to be imaged to produce a three dimensional image.

In an additional method to obtain an x-ray image performed consistent with the present invention, an object is placed in a device to record x-ray images, such as the device to record x-ray images as substantially described herein, power is applied to at least one of the plurality of cathodes of the x-ray source to generate x-ray radiation for a pre-set exposure time, the object is exposed to the x-ray radiation, and an x-ray image corresponding to the object is captured by either the x-ray detectors or the x-ray sensitive films of the device to record x-ray images.

In one aspect of the method, the power is applied to all of the plurality of cathodes simultaneously or to a a subset of the plurality of cathodes sequentially at a frequency. When applying power sequentially at a frequency, the x-ray detectors or the x-ray sensitive films can be moved and/or activated at a corresponding frequency to the power application frequency so as to capture the x-rays produced. The frequency can be in the range or 0.1 Hz to 100 kHz. Further, the frequency can be sufficiently rapid to dynamically image a physiological function, such as a beating heart.

In a still further aspect, the method provides an imaging environment in which the emitted x-rays are sufficiently discriminated with respect to the object to be imaged to produce a three dimensional image. This can be a result of the circumferential position and/or the elevation angle of incidence point with respect to the object to be imaged.

Variations of the above described method, as well as additional methods, are evident in light of the above described devices of the present invention.

While the present invention has been described by reference to the above-mentioned embodiments, certain modifications and variations will be evident to those of ordinary skill in the art. Therefore, the present invention is to limited only by the scope and spirit of the appended claims.

What is claimed is:

1. A system to generate and detect x-rays comprising:
  a cathode structure having a plurality of individually electrically addressable field emissive electron sources defining a plurality of cathodes, each cathode disposed on a first side of the cathode structure;
  a target structure having a deflection surface facing the first side of the cathode structure, the deflection surface defining a target;
  an object positioner disposed within an imaging zone; and
  a detector structure to receive and detect an x-ray from the target,
  wherein each cathode comprises a substrate and a gate electrode positioned parallel to and insulated from the substrate, the substrate comprising a field emissive material having an emitted electron current density of at least 1 mA/cm$^2$ when the cathode is subjected to an applied electrical field of at least 2V/$\mu$m, wherein the field emissive material is selected from the group consisting of single walled carbon nanotubes, double walled carbon nanotubes, multi-wall carbon nanotubes, nanotubes comprising at least one non-carbon element, or a nanorod/nanowire comprising at least one of a metal, a metal oxide, silicon, silicon carbide, silicon oxide, carbon nitride, boron nitride, boron carbide, or a chalcogenide.

2. The system of claim 1, wherein each of the plurality of cathodes is a recessed well in the cathode structure and into which the substrate is disposed, and the gate electrode is disposed across the surface of the substrate substantially equidistant from the substrate.

3. The system of claim 1, wherein the plurality of cathodes are each individually positioned on the first surface of the cathode structure at a predetermined interval.

4. The system of claim 3, wherein the predetermined interval is approximately 10° to 120°.

5. The system of claim 1, wherein the target is an area array of target material or a plurality of individual target material.

6. The system of claim 1, further comprising:
an evacuated chamber substantially in the form of a hollow cylinder having an inner wall and an outer wall and adapted to position an object to be imaged by the structure within the imaging zone.

7. The system of claim 6, further comprising:
a plurality of collimating windows disposed in the inner wall.

8. The system of claim 1, wherein the target is an area array of individual target material or a line array of target material.

9. The system of claim 1, wherein the detector is a charged-coupled device.

10. The system of claim 9, wherein the charge-coupled device is stationarily positioned to detect the x-ray.

11. The system of claim 1, wherein the cathode structure is stationary within the system.

12. The system of claim 1, wherein the field emissive electron sources are stationary within the system.

13. The system of claim 1, wherein an applied electrical field of greater than 2 V/$\mu$m produces a stable current density of at least about 100 mA/cm$^2$.

14. A method of generating an x-ray image comprising the steps of:
positioning an object within an imaging zone;
switching each of a plurality of cathodes on a cathode structure at a predetermined frequency to field emit an electron, each of the plurality of cathodes individually addressable and electrically switched in a programmable sequence to field emit electrons toward an incidence point on a target structure, each cathode comprising a field emissive electron source including a field emissive material having an emitted electron current density of at least 1 mA/cm$^2$ when the cathode is subjected to an applied electrical field of at least 2V/$\mu$m;
emitting an x-ray from a target of the target structure at the predetermined frequency;
imaging the object; and
detecting the emitted x-ray,
wherein a position on the target structure from which the x-ray emits corresponds spatially and temporally to a position on the cathode structure from which the electron emits,
wherein at least one of a circumferential position and an elevation angle of the emitted x-ray is sufficiently discriminated with respect to the object to produce a three dimensional image, and
wherein the field emissive material is selected from the group consisting of single walled carbon nanotubes, double walled carbon nanotubes, multi-wall carbon nanotubes, nanotubes comprising at least one non-carbon element, and nanorods/nanowires comprising at least one of a metal, a metal oxide, silicon, silicon carbide, silicon oxide, carbon nitride, boron nitride, boron carbide, or a chalcogenide.

15. The method of claim 14, wherein the predetermined frequency is in the range of 0.1 Hz to 100 kHz.

16. The method of claim 14, wherein the predetermined frequency is sufficiently rapid to dynamically image a physiological function.

17. The method of claim 14, wherein the electron is non-divergent and accelerated from a field emissive material toward a gate electrode and impacts the target at an incidence point.

18. The method of claim 14, wherein the step of emitting an x-ray forms a pencil-like x-ray beam, the x-ray beam corresponding to one or more pixels of a detecting means utilized in the step of detecting.

19. The method of claim 18, wherein the x-ray beam corresponds to no more than ten pixels.

20. The method of claim 14, wherein the step of emitting an x-ray forms a fan-like x-ray beam, the x-ray beam corresponding to one or more lines of pixels of a detecting means utilized in the step of detecting.

21. The method of claim 20, wherein the x-ray beam corresponds to a line of no more than ten lines of pixels.

22. The method of claim 14, wherein the step of emitting an x-ray forms a cone-like x-ray beam, the x-ray beam corresponding to an area of no more than 128×128 square pixels of a detecting means utilized in the step of detecting.

23. The method of claim 22, wherein the x-ray beam corresponds to an area of no more than 64×64 square pixels.

24. The method of claim 14, wherein a detecting means used in the step of detecting is a charge-coupled device.

25. The method of claim 24, wherein the charge-coupled device is stationarily positioned to detect the emitted x-ray.

26. The method of claim 14, further comprising a step of transferring a detected image resulting from the step of detecting to a computer storage device and refreshing a detecting means for a next image.

27. The method of claim 14, wherein the cathode structure is stationary with respect to the target structure.

28. The method of claim 14, wherein an applied electrical field of greater than 2 V/$\mu$m produces a stable current density of at least about 100 mA/cm$^2$.

29. A structure to generate x-rays comprising:
a plurality of individually electrically addressable electron sources defining a plurality of cathodes;
at least one target placed opposing the cathodes; and
an evacuated chamber that houses the plurality of cathodes and the at least one target,
wherein the electron sources are field emission electron sources,
wherein each electron field emission source is a triode-type comprising a field emissive material having an emitted electron current density of at least 1 mA/cm$^2$ when the cathode is subjected to an applied electrical field of at least 2V/$\mu$m and a gate electrode positioned parallel to and insulated from a substrate, wherein a plurality of electrons are field emitted from the cathode when the electric field between the gate electrode and the field emissive material exceeds a threshold value, wherein the plurality of field emitted electrons pass the gate electrode and are further accelerated to impact on the at least one target by an electric field applied between the gate electrode and the at least one target, wherein, upon impact, at an incidence point, at least one x-ray having a characteristic wavelength corresponding to a material of the at least one target and at least one x-ray having a continuous wavelength are generated, and wherein the field emissive material is selected from the group consisting of single walled carbon nanotubes, double walled carbon nanotubes, multi-wall carbon nanotubes, nanotubes comprising at least one non-carbon element, and nanorods/nanowires comprising at least one of a metal, a metal oxide, silicon, silicon carbide, silicon oxide, carbon nitride, boron nitride, boron carbide, or a chalcogenide.

30. The structure of claim 29, wherein the cathode structure is stationary within the structure to generate x-rays.

31. The structure of claim 29, wherein an applied electrical field of greater than 2 V/$\mu$m produces a stable current density of at least about 100 mA/cm$^2$.

32. A structure to generate x-rays comprising:

a plurality of individually electrically addressable electron sources defining a plurality of cathodes;

at least one target placed opposing the cathodes; and an evacuated chamber that houses the plurality of cathodes and the at least one target, wherein the electron sources are field emission electron sources comprising a field emissive material having an emitted electron current density of at least 1 m/Acm$^2$ when the cathode is subjected to an applied electrical field of at least 2V/$\mu$m, and the field emissive material is selected from the group consisting of single walled carbon nanotubes, double walled carbon nanotubes, multi-wall carbon nanotubes, nanotubes comprising at least one non-carbon element, and nanorods/nanowires comprising at least one of a metal, a metal oxide, silicon, silicon carbide, silicon oxide, carbon nitride, boron nitride, boron carbide, or a chalcogenide.

33. The structure of claim 32, wherein the field emissive material is coated on the substrate as a film, is embedded in a matrix of the substrate, or is a free-standing substrate structure, and the gate electrode is disposed across a surface of the substrate substantially equidistant from the substrate.

34. The structure of claim 32, further comprising:

an evacuated chamber with a plurality of x-ray transparent windows, each window positioned to allow the passage of at least one x-ray beam generated by a plurality of electrons from a corresponding one of the plurality of cathodes, wherein the plurality of cathodes and the at least one target are disposed within the evacuated chamber and the evacuated chamber is operationally maintained at a pressure lower than 10$^{-3}$ Torr.

35. The structure of claim 32, wherein the plurality of cathodes and the at least one target are each on an opposing plane and the target has a deflection surface that is oriented toward a surface of the plurality of cathodes that emits electrons.

36. The structure of claim 35, wherein the deflection surface is oriented non-parallel to the surface of the plurality of cathodes.

37. The structure of claim 35, wherein each of the plurality of cathodes are individually positioned on one of the opposing planes at a pre-determined interval.

38. The structure of claim 32, wherein the plurality of cathodes are disposed on a first ring and the at least one target is disposed on a second ring, the first and second rings concentric, and the at least one target has a deflection surface that is oriented toward a surface of the plurality of cathodes that emits electrons.

39. The structure of claim 38, wherein the deflection surface is oriented non-parallel to the surface of the plurality of cathodes.

40. The structure of claim 38, wherein each of the plurality of cathodes are individually positioned on one of the first or second rings at a pre-determined interval.

41. The method of claim 32, wherein the cathode structure is stationary within the structure to generate x-rays.

42. The structure of claim 32, wherein an applied electrical field of greater than 2 V/$\mu$m produces a stable current density of at least about 100 mA/cm$^2$.

43. A device to record x-ray images, comprising:

an x-ray source comprising a plurality of individually electrically addressable electron sources defining a plurality of cathodes, the plurality of cathodes disposed on a face of a first planar surface, at least one target disposed on a second planar surface, a deflection surface of the second planar surface opposing the face of the first planar surface, and an evacuated chamber that houses the plurality of cathodes and the at least one target;

an array or matrix of x-ray detectors or x-ray sensitive films opposing the x-ray source, the array or matrix substantially parallel to and at equal distance to the x-ray source; and an object positioner placed between the x-ray source and the array or matrix, wherein the plurality of cathodes includes a field emissive material having an emitted electron current density of at least 1 mA/cm$^2$ when the cathode is subjected to an applied electrical field of at least 2V/$\mu$m selected from the group consisting of single walled carbon nanotubes, double walled carbon nanotubes, multi-wall carbon nanotubes, nanotubes comprising at least one non-carbon element, or a nanorod/nanowire comprising at least one of a metal, a metal oxide, silicon, silicon carbide, silicon oxide, carbon nitride, boron nitride, boron carbide, or a chalcogenide.

44. The device of claim 43, wherein the deflection surface is oriented substantially parallel to the face of the plurality of cathodes that emits electrons.

45. The device of claim 43, wherein each of the plurality of electron sources are individually positioned at a pre-determined interval on the face of the plurality of cathodes.

46. The device of claim 43, wherein the x-ray source further comprises a plurality of x-ray transparent windows disposed in a wall of the evacuated chamber, and a plurality of parallel collimators, at least one parallel collimator on each one of the plurality of x-ray transparent windows.

47. The device of claim 43, wherein the object positioner is movable with respect to the x-ray source.

48. The device of claim 43, wherein the detector is a charged coupled device.

49. The device of claim 48, wherein the detector is stationary with respect to the x-ray source.

50. The device of claim 43, wherein the plurality of electron sources are stationary within the x-ray source.

51. The device of claim 43, wherein an applied electrical field of greater than 2 V/$\mu$m produces a stable current density of at least about 100 mA/cm$^2$.

52. A method to obtain an x-ray image, the method comprising:

placing an object in an x-ray source, the x-ray source comprising a plurality of individually electrically addressable electron sources defining a plurality of cathodes, the plurality of cathodes disposed on a face of a first planar surface, at least one target disposed on a second planar surface, a deflection surface of the second planar surface opposing the face of the first planar surface, and an evacuated chamber that houses the plurality of cathodes and the at least one target, an array or matrix of x-ray detectors or x-ray sensitive films opposing the x-ray source, the array or matrix substantially parallel to and at equal distance to the x-ray source, and an object positioner placed between the x-ray source and the array or matrix;

applying power to at least one of the plurality of cathodes to generate x-ray radiation for a pre-set exposure time;

exposing the object to the x-ray radiation; and capturing an x-ray image corresponding to the object by either the x-ray detectors or the x-ray sensitive films, wherein the plurality of cathodes includes a field emissive material having an emitted electron current density of at least 1 mA/cm$^2$ when the cathode is subjected to an applied electrical field of at least 2V/$\mu$m selected from the group consisting of single walled carbon nanotubes, double walled carbon nanotubes, multi-wall carbon nanotubes, nanotubes comprising at least one non-carbon element, or a nanorod/nanowire comprising at least one of a metal, a metal oxide, silicon, silicon carbide, silicon oxide, carbon nitride, boron nitride, boron carbide, or a chalcogenide.

53. The method of claim 52, wherein the power is applied to all of the plurality of cathodes simultaneously.

54. The method of claim 52, wherein the power is applied to a subset of the plurality of cathodes sequentially at a pre-set or variably-set frequency.

55. The method of claim 54, further comprising: moving or activating the x-ray detectors or the x-ray sensitive films at a corresponding frequency to the pre-set or variably-set frequency to capture the x-ray image.

56. The method of claim 52, wherein a detecting means used in the step of detecting is a charge-coupled device.

57. The method of claim 56, wherein the charge-coupled device is stationarily positioned to detect the emitted x-ray.

58. The method of claim 52, further comprising a step of transferring a detected image resulting from the step of detecting to a computer storage device and refreshing a detecting means for a next image.

59. The method of claim 52, wherein the plurality of electron sources are stationary within the x-ray source.

60. The method of claim 52, wherein an applied electrical field of greater than 2 V/$\mu$m produces a stable current density of at least about 100 mA/cm$^2$.

61. A device to generate x-ray images comprising:

an x-ray source comprising a plurality of individually electrically addressable electron sources defining a plurality of cathodes, the plurality of cathodes disposed on a surface of a first ring, at least one target disposed on a second ring, a deflection surface of the second ring opposing the surface of the first ring, and an evacuated chamber that houses the plurality of cathodes and the at least one target;

an array or matrix of x-ray detectors or x-ray sensitive films on a surface opposing the x-ray source, the array or matrix substantially concentric to and at equal distance to the x-ray source; and an object positioner placed between the x-ray source and the array or matrix, wherein the plurality of cathodes includes a field emissive material having an emitted electron current density of at least 1 mA/cm$^2$ when the cathode is subjected to an applied electrical field of at least 2V/$\mu$m selected from the group consisting of single walled carbon nanotubes, double walled carbon nanotubes, multi-wall carbon nanotubes, nanotubes comprising at least one non-carbon element, or a nanorod/nanowire comprising at least one of a metal, a metal oxide, silicon, silicon carbide, silicon oxide, carbon nitride, boron nitride, boron carbide, or a chalcogenide.

62. The device of claim 61, wherein the first and second ring are concentric.

63. The device of claim 61, wherein each of the plurality of electron sources are individually positioned at a pre-determined interval on the surface of the ring.

64. The device of claim 61, wherein the x-ray source further comprises a plurality of x-ray transparent windows disposed in a wall of the evacuated chamber and a plurality of parallel collimators, at least one parallel collimator on each one of the plurality of x-ray transparent windows.

65. The device of claim 61, wherein the object positioner is movable with respect to the x-ray source.

66. The device of claim 61, wherein the detector is a charged coupled device.

67. The device of claim 66, wherein the charge-coupled device is stationarily positioned to detect the x-ray.

68. The device of claim 61, wherein the plurality of electron sources are stationary within the x-ray source.

69. The device of claim 61, wherein an applied electrical field of greater than 2 V/$\mu$m produces a stable current density of at least about 100 mA/cm$^2$.

70. A method to obtain an x-ray image, the method comprising:

placing an object in an x-ray source, the x-ray source comprising a plurality of individually electrically addressable electron sources defining a plurality of cathodes, the plurality of cathodes disposed on a surface of a first ring, at least one target disposed on a second ring, a deflection surface of the second ring opposing the surface of the first ring, and an evacuated chamber that houses the plurality of cathodes and the at least one target, an array or matrix of x-ray detectors or x-ray sensitive films on a surface opposing the x-ray source, the array or matrix substantially concentric to and at equal distance to the x-ray source, and an object positioner placed between the x-ray source and the array or matrix;

applying power to all of the plurality of cathodes to generate x-ray radiation for a pre-set exposure time;

exposing the object to the x-ray radiation; and capturing an x-ray image corresponding to the object by either the x-ray detectors or the x-ray sensitive films, wherein the plurality of cathodes includes a field emissive material having an emitted electron current density of at least 1 mA/cm$^2$ when the cathode is subjected to an applied electrical field of at least 2V/$\mu$m selected from the group consisting of single walled carbon nanotubes, double walled carbon nanotubes, multi-wall carbon nanotubes, nanotubes comprising at least one non-carbon element, or a nanorod/nanowire comprising at least one of a metal, a metal oxide, silicon, silicon carbide, silicon oxide, carbon nitride, boron nitride, boron carbide, or a chalcogenide.

71. The method of claim 70, wherein the power is applied to all of the plurality of cathodes simultaneously.

72. The method of claim 70, wherein the power is applied to a subset of the plurality of cathodes sequentially at a pre-set or variably-set frequency.

73. The method of claim 72, further comprising:

moving or activating the x-ray detectors or the x-ray sensitive films at a corresponding frequency to the pre-set or variably-set frequency to capture the x-ray image.

74. The method of claim 70, wherein a detecting means used in the step of capturing an x-ray image is a charge-coupled device.

75. The method of claim 74, wherein the charge-coupled device is stationarily positioned to detect the x-ray radiation.

76. The method of claim 70, further comprising a step of transferring a detected image resulting from the step of capturing an x-ray image to a computer storage device and refreshing a detecting means for a next x-ray image.

77. The method of claim 70, wherein the plurality of electron sources are stationary within the x-ray source.

78. The method of claim 70, wherein an applied electrical field of greater than 2 V/$\mu$m produces a stable current density of at least about 100 mA/cm$^2$.

* * * * *